United States Patent
Brown et al.

(10) Patent No.: US 10,407,716 B2
(45) Date of Patent: Sep. 10, 2019

(54) ELECTRONIC PLATFORM FOR SENSING AND CONTROL OF ELECTROCHEMICAL REACTIONS

(71) Applicant: Duke University, Durham, NC (US)

(72) Inventors: April S. Brown, Durham, NC (US); Maria Losurdo, Durham, NC (US); Chris Dwyer, Durham, NC (US)

(73) Assignee: Duke University, Durham, NC (US)

( * ) Notice: Subject to any disclaimer, the term of this patent is extended or adjusted under 35 U.S.C. 154(b) by 69 days.

(21) Appl. No.: 15/125,473

(22) PCT Filed: Mar. 13, 2015

(86) PCT No.: PCT/US2015/020406
§ 371 (c)(1),
(2) Date: Sep. 12, 2016

(87) PCT Pub. No.: WO2015/187227
PCT Pub. Date: Dec. 10, 2015

(65) Prior Publication Data
US 2017/0088883 A1    Mar. 30, 2017

Related U.S. Application Data

(60) Provisional application No. 61/967,248, filed on Mar. 13, 2014.

(51) Int. Cl.
*G01N 27/327*    (2006.01)
*C12Q 1/6825*    (2018.01)
(Continued)

(52) U.S. Cl.
CPC ......... *C12Q 1/6825* (2013.01); *G01N 27/125* (2013.01); *G01N 27/3275* (2013.01); *G01N 27/72* (2013.01); *G01N 27/4141* (2013.01)

(58) Field of Classification Search
None
See application file for complete search history.

(56) References Cited

U.S. PATENT DOCUMENTS 4,827,320 A * 5/1989 Morkoc ................ H01L 29/205
257/18
5,370,769 A * 12/1994 Kadomura ........ H01L 21/30621
257/E21.222
(Continued)

FOREIGN PATENT DOCUMENTS

EP    1801886    6/2007
EP    2019318    1/2009
(Continued)

OTHER PUBLICATIONS

Addison, A.W. et al., "Hemoglobin: autoreduction and spectroscopy," Biochem. (1986) 25:4104-4113.
(Continued)

*Primary Examiner* — Eli S Mekhlin
(74) *Attorney, Agent, or Firm* — Michael Best & Friedrich LLP

(57) ABSTRACT

A sensor comprising a semiconductor layer having a two dimensional electron gas (2DEG) and an oxide layer in electronic contact with the semiconductor layer is provided. A method of detecting an analyte molecule using such sensor is also provided.

17 Claims, 11 Drawing Sheets

(51) Int. Cl.
  *G01N 27/12* (2006.01)
  *G01N 27/72* (2006.01)
  *G01N 27/414* (2006.01)

(56) References Cited

U.S. PATENT DOCUMENTS

| | | | |
|---|---|---|---|
| 5,567,301 A | 10/1996 | Stetter et al. | |
| 5,603,820 A | 2/1997 | Malinski et al. | |
| 5,674,700 A | 10/1997 | Maurel | |
| 6,144,040 A | 11/2000 | Ashton | |
| 6,329,209 B1 | 12/2001 | Wagner et al. | |
| 6,365,418 B1 | 4/2002 | Wagner et al. | |
| 6,384,321 B1* | 5/2002 | Mikoshiba | H01G 9/2004 136/256 |
| 6,433,356 B1 | 8/2002 | Cahen et al. | |
| 6,647,796 B2 | 11/2003 | Beach et al. | |
| 6,682,942 B1 | 1/2004 | Wagner et al. | |
| 6,716,620 B2 | 4/2004 | Bashir et al. | |
| 6,780,582 B1 | 8/2004 | Wagner et al. | |
| 6,896,872 B2 | 5/2005 | Dambinova | |
| 6,897,073 B2 | 5/2005 | Wagner et al. | |
| 7,144,705 B2 | 12/2006 | Hochstrasser et al. | |
| 7,247,469 B2 | 7/2007 | Wagner et al. | |
| 7,341,692 B2 | 3/2008 | Willett et al. | |
| 7,361,946 B2 | 4/2008 | Johnson et al. | |
| 7,427,490 B2 | 9/2008 | Valkirs et al. | |
| 7,504,658 B2 | 3/2009 | Kunze et al. | |
| 7,868,354 B2 | 1/2011 | Garcia et al. | |
| 8,828,713 B2 | 9/2014 | Ren et al. | |
| 2003/0036054 A1 | 2/2003 | Ladisch et al. | |
| 2003/0059954 A1 | 3/2003 | Vikholm et al. | |
| 2003/0096331 A1 | 5/2003 | Dambinova | |
| 2003/0138829 A1 | 7/2003 | Unger et al. | |
| 2003/0148404 A1 | 8/2003 | Michaelson | |
| 2003/0197503 A1 | 10/2003 | Kawano et al. | |
| 2003/0199000 A1 | 10/2003 | Valkirs et al. | |
| 2004/0072360 A1 | 4/2004 | Naaman et al. | |
| 2004/0115711 A1 | 6/2004 | Su et al. | |
| 2004/0157281 A1 | 8/2004 | Hulkower et al. | |
| 2004/0159836 A1 | 8/2004 | Sugimoto et al. | |
| 2005/0097941 A1 | 5/2005 | Sandvik et al. | |
| 2006/0046259 A1 | 3/2006 | Baird et al. | |
| 2006/0166303 A1 | 7/2006 | Spanuth | |
| 2006/0172341 A1 | 8/2006 | Dambinova | |
| 2006/0172342 A1 | 8/2006 | Dambinova | |
| 2006/0267570 A1 | 11/2006 | Arkin | |
| 2006/0281135 A1 | 12/2006 | Dambinova | |
| 2007/0264623 A1 | 11/2007 | Wang et al. | |
| 2008/0081326 A1 | 4/2008 | Amano | |
| 2008/0204043 A1 | 8/2008 | Wang et al. | |
| 2009/0057650 A1 | 3/2009 | Lieber et al. | |
| 2009/0085071 A1 | 4/2009 | Brongersma et al. | |
| 2009/0306578 A1 | 12/2009 | Sivan et al. | |
| 2010/0012977 A1* | 1/2010 | Derluyn | H01L 29/2003 257/194 |
| 2010/0188069 A1* | 7/2010 | Ren | G01N 33/54306 324/71.5 |
| 2011/0068372 A1 | 3/2011 | Ren et al. | |
| 2011/0088456 A1* | 4/2011 | Ren | G01N 33/005 73/31.06 |
| 2011/0199102 A1* | 8/2011 | Garcia | G01N 27/4148 324/658 |
| 2012/0058488 A1 | 3/2012 | Sheppard et al. | |
| 2012/0122736 A1 | 5/2012 | Angelo et al. | |
| 2013/0288378 A1 | 10/2013 | Gu et al. | |
| 2014/0048796 A1* | 2/2014 | Baek | H01L 29/778 257/43 |
| 2015/0021510 A1* | 1/2015 | Zenitani | H01B 1/08 252/62.2 |

FOREIGN PATENT DOCUMENTS

| | | |
|---|---|---|
| WO | WO 1993/008464 | 4/1993 |
| WO | WO 02/48701 | 6/2002 |
| WO | WO 03/102546 | 12/2003 |
| WO | WO 2005/124345 | 12/2005 |
| WO | WO 2007/015113 | 2/2007 |
| WO | WO 2007/092909 | 8/2007 |
| WO | WO 2007/114947 | 10/2007 |
| WO | WO 2007/124439 | 11/2007 |
| WO | WO 2008/008349 | 1/2008 |
| WO | WO 2008/008846 | 1/2008 |
| WO | WO 2008/105824 | 9/2008 |
| WO | WO 2010/005738 | 1/2010 |
| WO | WO 2010/096331 | 8/2010 |
| WO | WO 2011/046858 | 4/2011 |
| WO | WO 2013/039819 | 3/2013 |

OTHER PUBLICATIONS

Allard, L. et al., "Park7 and nucleoside diphosphate kinase as a plasma markers for the early diagnosis of stroke," Clin. Chem. (2005) 51:2043-2051.

Angelo et al., "Interaction of NO with hemoglobin: from microbes to man," Methods Enzym. (2008) 436:125-158.

Ashkenasy, G. et al., "Molecular engineering of semiconductor surfaces and devices," Acc. Chem. Res. (2002) 35:121-128.

Battut, V. et al., "Gas sensitivity of InP epitaxial thin layers," Sensors and Actuators B (1997) 44:503-506.

Bayer, M. et al., "Theoretical study of electrolyte gate AIGaN/GaN field effect transistors," Appl. Phys. Lett. (2005) 97:033703, 6 pages.

Bedioui, F. et al., "Electrochemical nitric oxide sensors for biological samples—principle, selected examples and applications," Electroanalysis (2003) 15:5-18.

Bell, G.R. et al., "Accumulation layer profiles at InAs polar surfaces," Applied Phys. Lett. (1997) 71:3688-3690.

Cahen, D. et al., "The cooperative molecular field effect," Adv. Funct. Mater. (2005) 15:1571-1578.

Castellanos, M. et al., "Applicability of biomarkers in ischemic stroke," Cerebrovasc. Dis. (2007) 24 Suppl 1:7-15.

Castillo, J. et al., "The release of tumor necrosis factor-alpha is associated with ischemic tolerance in human stroke," Ann. Neurol. (2003) 54:811-819.

Culotta, E. et al., "NO news is good news," Science (1992) 258(5090):1862-1865.

Dahlen, J., "A novel panel of markers to diagnose stroke," Proceedings of the 10th Asian Pacific Congress of Clinical Biochemistry in conjunction with the Australasian Association of Clinical Biochemists' 42 Annual Scientific Conference, published in Clinical Biochem. Rev. (2004) 25(Suppl):S18-S128.

Dambinova, S.A. et al., "Multiple panel of biomarkers for tia/stroke evaluation," Stroke (2002) 33:1181-1182.

Eickhoff, M. et al., "Electronics and sensors-based on pyroelectric AIGaN/GaN heterostructures; Part B: sensor applications," Phys. Stat. Sol. (2003) 6:1908-1918.

Flechtner, K. et al., "No-induced reversible switching of the electronic interaction between a porphyrin-coordinated cobalt ion and a silver surface," J. Am. Chem. Soc. (2007) 129:12110-12111.

Freed, M. et al., "Real time in-situ data acquisition using autonomous on-wafer sensor arrays," in ISSM (2000) Tokyo, Japan.

Garcia, M. et al., "Functionalization and characterization of InAs and InP surfaces with hemin," J. Vac. Sci. Technol. (2007) 25:1504-1510.

Garcia, M.A. et al., "Comparison of functionalized III-V semiconductor response for nitric oxide," Sensor Letters (2008) 6:627-634.

Garcia, M.A. et al., "Impact of porphyrin functional groups on InAs gas sensors," (Nov. 5, 2007) 21 pages, Retrieved from the Internet: http://nanohub.org/resources/3149/download/2007.07.19-garcia.mcw.pdf.

Gaston, B., "Nitric oxide and thiol groups," Biochim. Biophys. Acta. (1999) 1411:323-333.

Gomez, R. et al., "Instrumentation system for in vivo organ studies," IEEE (2001) 1:261-264.

Gow, A.J. et al., "Reactions between nitric oxide and haemoglobin under physiological conditions," Nature (1998) 391:169-173.

(56) References Cited

OTHER PUBLICATIONS

Gow, A.J. et al., "The oxyhemoglobin reaction of nitric oxide," Proc. Natl. Acad. Sci. USA (1999) 96:9027-9032.
Haga, Y. et al., "Biomedical microsystems for minimally invasive diagnosis and treatment," Proceedings of IEEE (2004) 92:98-114.
Herold, S. et al., "Mechanistic studies of S-nitrosothiol formation by NO*/O2 and by NO*/methemoglobin," Arch. Biochem. Biophys. (2005) 436:386-396.
Hess, D.T. et al., "Protein s-nitrosylation: purview and parameters," Nat. Rev. Mol. Cell Biol. (2005) 6:150-166.
Jauch, E.C. et al., "Can d-dimer levels identify patients at risk for early neurological deterioration in acute ischemic stroke?" Nature Clin. Pract. Neurol. (2006) 2:590-591.
Jia et al., "S-nitrosohaemoglobin: a dynamic activity of blood involved in vascular control," Nature (1996) 380:221-226.
Kadish, K.M. et al., editors, Applications: Past, Present and Future. The Porphyrin Handbook, Academic Press: San Diego, CA (1999) vol. 6, pp. 240-250 (cover and table of contents only).
Katzan, I.L. et al., "Utilization of intravenous tissue plasminogen activator for acute ischemic stroke," Arch. Neurol. (2004) 61:346-350.
Kim, J.S. et al., "Serial measurement of interleukin-6, transforming growth factor-beta, and s-100 protein in patients with acute stroke," Stroke (1996) 27:1553-1557.
Kirchner, C. et al., "Corrosion protection and long-term chemical functionalization of gallium arsenide in an aqueous environment," Adv. Funct. Mat. (2002) 12(4):266-276.
Kruszyna, R. et la., "Nitrite conversion to nitric oxide in red cells and its stabilization as a nitrosylated valency hybrid of hemoglobin," J. Pharm. Exp. Thera. (1987) 241:307-313.
Kumar, K., "Overview: use of biomarkers for early diagnosis of ischemic stroke," Cuff. Opin. Invest. Drugs (2005) 6:21-24.
Lantoine, F. et al., "Selective and sensitive electrochemical measurement of nitric-oxide in aqueous-solution discussion and new results," J. Electroanal. Chem. (1995) 392:85-89.
Laskowitz, D.T. et al., "Clinical usefulness of a biomarker-based diagnostic test for acute stroke: the biomarker rapid assessment in ischemic injury (brain) study," Stroke (2009) 40:77-85.
Laskowitz, D.T. et al., "Serum markers of cerebral ischemia," Journal of Stroke and Cerebrovascular Diseases: the Official Journal of National Stroke Association (1998) 7:234-241.
Lu, H. et al., "High temperature hall effect sensors based on AlGaN/GaN heterojunctions," J. Appl. Phys. (2006) 99:114510-1-114510-4.
Luchsinger, B.P. et al., "Assessments of the chemistry and vasodilatory activity of nitrite with hemoglobin under physiologically relevant conditions," J. Inorg. Biochem. (2005) 99:912-921.
Luchsinger, B.P. et al., "Routes to S-nitrosohemoglobin formation with heme redox and preferential reactivity in the beta subunits," Proc. Natl. Acad. Sci. USA (2003) 100:461-566.
McGirt, M.J. et al., "Serum von willebrand factor, mastrix metalloproteinase-9, and vascular endothelial growth factor levels predict the onset of cerebral vasospasm after aneurysmal subarachnoid hemorrhage," Neurosurg. (2002) 51:1128-1134, discussion 1134-1135.
McMahon, T.J. et al., "Extrapulmonary effects of inhaled nitrix oxide: role of reversible S-nitrosylation of erythrocytic hemoglobin," Proc. Am. Thorac. Soc. (2006) 3:153-160.
McMahon, T.J. et al., "Nitric oxide in the human respiratory cycle," Nat. Med. (2002) 8:711-717.
Montaner, J. et al., "Etiologic diagnosis of ischemic stroke subtypes with plasma biomarkers," Stroke (2008) 39:2280-2287.
Montaner, J. et al., "Matrix metalloproteinase-9 pretreatment level predicts intracranial hemorrhagic complications after thrombolysis in human stroke," Circul. (2003) 107:598-603.
Montaner, J., "Stroke biomarkers: can they help us to guide stroke thrombolysis?" Drug News Perspect. (2006) 19:523-532.
Moore, E.G. et al., "Cooperativitiy in the dissociation of nitric oxide from hemoglobin," J. Biol. Chem. (1976) 251:2788-2794.
Muir, K.W. et al., "C-reactive protein and outcome after ischemic stroke," Stroke (1999) 30:981-985.
Potter, W., "Reduction of nitric oxide to nitrous oxide by cobalt porphyrins and corrins," Fuel Proces. Tech. (1994) 40:355-360.
Reynolds, M.A. et al., "Early biomarkers of stroke," Clin. Chem. (2003) 49:1733-1739.
Rovira, C. et al., "Equilibrium geometries and electronic structure of iron-porphyrin complexes: a density functional study," J. Phys. Chem. A. (1997) 101:8914-8925.
Seripa, D. et al., "Relevance of interleukin-1 receptor antagonist intron-2 polymorphism in ischemic stroke," Cerebrovasc. Dis. (2003) 15:276-281.
Sharma, V.S. et al., "Reaction of nitric oxide with heme proteins and model compounds of hemoglobin," Biochem. (1987) 26:3837-3843.
Sharma, V.S. et al., "The dissociation of NO from nitrosylhemoglobin," J. Biol. Chem. (1978) 253:6467-6472.
Ship, N.J. et al., "Rates of release of nitric oxide from HbSNO and internal electron transfer," Bioorg. Chem. (2003) 31:3-10.
Singel et al., "Chemical physiology of blood flow regulation by red blood cels," Annu. Rev. Physiol. (1997) 67:99-145.
Smith, R.P., "Chemicals reacting with various forms of hemoglobin: biological significance, mechanisms, and determination," J. For. Sci. (1991) 36:662-672.
Squizzato, A. et al., "D-dimer testing in ischemic stroke and cerebral sinus and venous thrombosis," Seminars in Vascular Medicine (2005) 5:379-386.
Stamler et al., Blood flow regulation by S-nitrosohemoglobin in the physiological oxygen gradient, Science (1997) 276:2034-2037.
Steinhoff, G. et al., "pH response for GaN surfaces and its application for pH-sensitive field-effect transistors," Appl. Phys. Lett. (2003) 83(1):177-179.
Stutzmann, M. et al., "GaN-based heterostructures for sensor applications," Dia. Related Matt. (2002) 11:886-891.
Taj, F. et al., "Inflammatory biomarkers of stroke," JPMA The Journal of the Pakistan Medical Assoc. (2007) 57:381-382.
Taketa, F. et al., "Chain nonequivalence in binding of nitric oxide to hemoglobin," J. Biol. Chem. (1978) 253:5448-5451.
Talazac, L. et al., "Air quality evaluation by monolithic InP-based resistive sensors," Sensors and Actuators B: Chemical (2001) 76:258-264.
Talazac, L. et al., "Gas sensing properties of pseudo-Schottky diodes on p-type indium phosphide substrates application to O3 and NO2 monitoring in urban ambient air," Sensors and Actuators B: Chemical (2002) 83:149-159.
Tarkowski, E. et al., "Early intrathecal production of interleukin-6 predicts the size of brain lesion in stroke," Stroke (1995) 26:1393-1398.
Tsui, D.C., "Electron-tunneling studies of a quantized surface accumulation layer," Phys. Rev. B. (1971) 4(12):4438-4449.
Uhlrich, J. et al., "Interfacial chemistry and energy band line-up of pentacene with the GaN (0001) surface," J. Crys. Grow. (2007) 300:204-211.
Viktorovitch, P. et al., "Electronic Properties of InAs Surface Quantum Wells Grown on InP(100)," Second International Conference, Denver, Colorado (Apr. 23-25, 1990) 148-152.
Vilan, A. et al., "How organic molecules can control electronic devices," Trends in Biotech. (2002) 20:22-29.
Wang, D.Z. et al., "Treating acute stroke patients with intravenous tpa. The osf stroke network experience," Stroke (2000) 31:77-81.
Welch, W.J., "Heat shock proteins as biomarkers for stroke and trauma," Am. J. Med. (2001) 111:669-670.
Whiteley, W. et al., "Blood biomarkers in the diagnosis of ischemic stroke: a systematic review," Stroke (2008) 39:2902-2909.
Wierzbowska, K. et al., "Studies of gas sensing, electrical and chemical properties of n-Inp epitaxial surfaces," Physica status Solidi(a) (2006) 203(9):2281-2286.
Wolter, S.D. et al., "Porphyrisation of III-V compound semiconductor surfaces for detection of exhaled breath indicators of physiological status," Keynote lecture at SMCBS' 2007 International Workshop, See online Journal of SMCBS' 2007 International Workshop, 2 pages.

(56) References Cited

OTHER PUBLICATIONS

Wu, D.G. et al., "Direct detection of low-concentration NO in physiological solutions by a new GaAs-based sensor," Chem. Eur. J. (2001) 7(8):1743-1749.
Zhao, Y. et al., "Thionitroxides, RSNHO: the structure of the SNO moiety in 'S-nitrosohemoglobin' a possible NO reservoir and transporter," J. Am. Chem. Soc. (2006) 128, 1422-1423.
United States Patent Office Action for U.S. Appl. No. 11/937,375 dated Apr. 27, 2010 (8 pages).
United States Patent Office Action for U.S. Appl. No. 11/937,375 dated Jun. 17, 2010 (4 pages).
United States Patent Notice of Allowance for U.S. Appl. No. 11/937,375 dated Jul. 9, 2010 (5 pages).
United States Patent Office Action for U.S. Appl. No. 12/948,946 dated Feb. 1, 2012 (7 pages).
United States Patent Office Action for U.S. Appl. No. 12/948,946 dated Aug. 27, 2012 (8 pages).
United States Patent Office Action for U.S. Appl. No. 12/999,262 dated Oct. 28, 2013 (9 pages).
United States Patent Office Action for U.S. Appl. No. 13/201,181 dated Oct. 19, 2012 (13 pages).
United States Patent Office Action for U.S. Appl. No. 13/201,181 dated Sep. 11, 2013 (20 pages).
International Search Report and Written Opinion for Application No. PCT/US2009/047546 dated Nov. 2, 2009 (11 pages).
Invitation to Pay Additional Fees for Application No. PCT/US2009/047546 dated Jul. 28, 2009 (2 pages).
United States Patent Office Action for U.S. Appl. No. 12/999,262 dated Mar. 26, 2015 (9 pages).
United States Patent Office Final Action for U.S. Appl. No. 12/999,262 dated Sep. 4, 2015 (10 pages).
United States Patent Office Action for U.S. Appl. No. 13/201,181 dated Oct. 26, 2015 (9 pages).
International Search Report and Written Opinion for Application No. PCT/US2015/020406 dated Jan. 14, 2016 (8 pages).
United States Patent Office Final Action for U.S. Appl. No. 13/201,181 dated Jun. 16, 2016 (9 pages).
United States Patent Office Action for U.S. Appl. No. 12/999,262 dated Nov. 14, 2016 (11 pages).
United States Patent Office Action for U.S. Appl. No. 13/201,181 dated Jan. 9, 2017 (13 pages).
United States Patent Office Notice of Allowance for U.S. Appl. No. 12/999,262 dated Apr. 3, 2017 (9 pages).
United States Patent Office Action for U.S. Appl. No. 13/201,181 dated May 26, 2017 (4 pages).
Pearton, S.J. et al., "GaN-based diodes and transistors for chemical, gas, biological and pressure sensing," J. Phys. Condens. Matter (2004) 16:R961-R994.
United States Patent Office Action for U.S. Appl. No. 11/937,375 dated Aug. 24, 2009 (7 pages).
International Search Report and Written Opinion for Application No. PCT/US2010/023917 dated Jun. 14, 2010 (16 pages).
United States Patent .Office Action for U.S. Appl. No. 12/999,262 dated May 29, 2014 (10 pages).
United States Patent Office Notice of Allowance for U.S. Appl. No. 13/201,181 dated Dec. 21, 2017 (7 pages).
United States Patent Office Notice of Allowance for U.S. Appl. No. 12/999,262 dated Feb. 2, 2018 (6 pages).

* cited by examiner

ELECTRONIC PLATFORM FOR SENSING AND CONTROL OF ELECTROCHEMICAL REACTIONS

CROSS-REFERENCE TO RELATED APPLICATIONS

This application claims the benefit of priority to U.S. Provisional Patent Application Ser. No. 61/967,248 filed Mar. 13, 2014, which is incorporated herein by reference in its entirety.

STATEMENT OF GOVERNMENT SUPPORT

This invention was made with government support under grant number N66001-09-C-2082 awarded by DARPA. The government has certain rights in the invention.

BACKGROUND

The present invention relates generally to a sensor and method for sensing and controlling surface-based chemical reactions on an electronic platform which possesses a native surface-confined two-dimensional electron gas (2DEG).

Biological and chemical sensor systems are of great importance in health care, industrial processing, environmental monitoring and remediation, energy production, and national defense. The ideal chemical sensor would have one or more of the following characteristics: (1) fast response, (2) high sensitivity, (3) high selectivity, (4) capability for detecting and recognizing as many chemicals as possible, (5) low power consumption (e.g., not relying on ionization or vaporization) and (6) small, lightweight, compact, (7) easy to use, and (8) inexpensive.

SUMMARY

In one aspect, the invention provides a sensor. The sensor includes a semiconductor layer having a two dimensional electron gas (2DEG); and an oxide layer in electronic contact with the semiconductor layer. In one embodiment, the semiconductor layer includes type III-V material including, but not limited to, Indium (In), Nitrogen (N), Phosphorus (P), and Arsenic (As). Suitably, the 2DEG is present at the interface of the semiconductor layer and the oxide layer. In another embodiment, the senor further includes an electronic circuit electronically coupled to the semiconductor layer, the electronic circuit measuring the electron density of the 2DEG, the electron mobility of the 2DEG, or combinations thereof. In another embodiment, the oxide layer includes a functionalizing molecule, such as an oligonucleotide, a peptide, a polypeptide, a protein, a polymer, or a combination thereof.

In another aspect, the invention provides a method detecting an analyte molecule. The method includes the steps of providing a sensor comprising (a) a semiconductor layer having a two dimensional electron gas (2DEG), and (b) an oxide layer in electronic contact with the semiconductor layer; making a first measurement of an electrical property of the 2DEG; contacting the analyte molecule with the oxide layer of the sensor; subsequently making a second measurement of the electrical property of the 2DEG; wherein the difference between the first and second measurement of electrical property of the 2DEG indicates the presence of the analyte molecule. In one embodiment, the electrical property is selected from the group consisting of the electron density of the 2DEG, the electron mobility of the 2DEG, and combinations thereof. In another embodiment, the electrical property of the 2DEG is measured by a Hall bar device.

The method of the present invention may be used to detect an analyte molecule, such as a nucleic acid and a protein molecule, in a fluid. For example, the method of the present invention can be used to determine the concentration or the conformation of the analyte molecule.

Other aspects of the invention will become apparent by consideration of the detailed description and accompanying drawings.

DETAILED DESCRIPTION

Figure 1A:
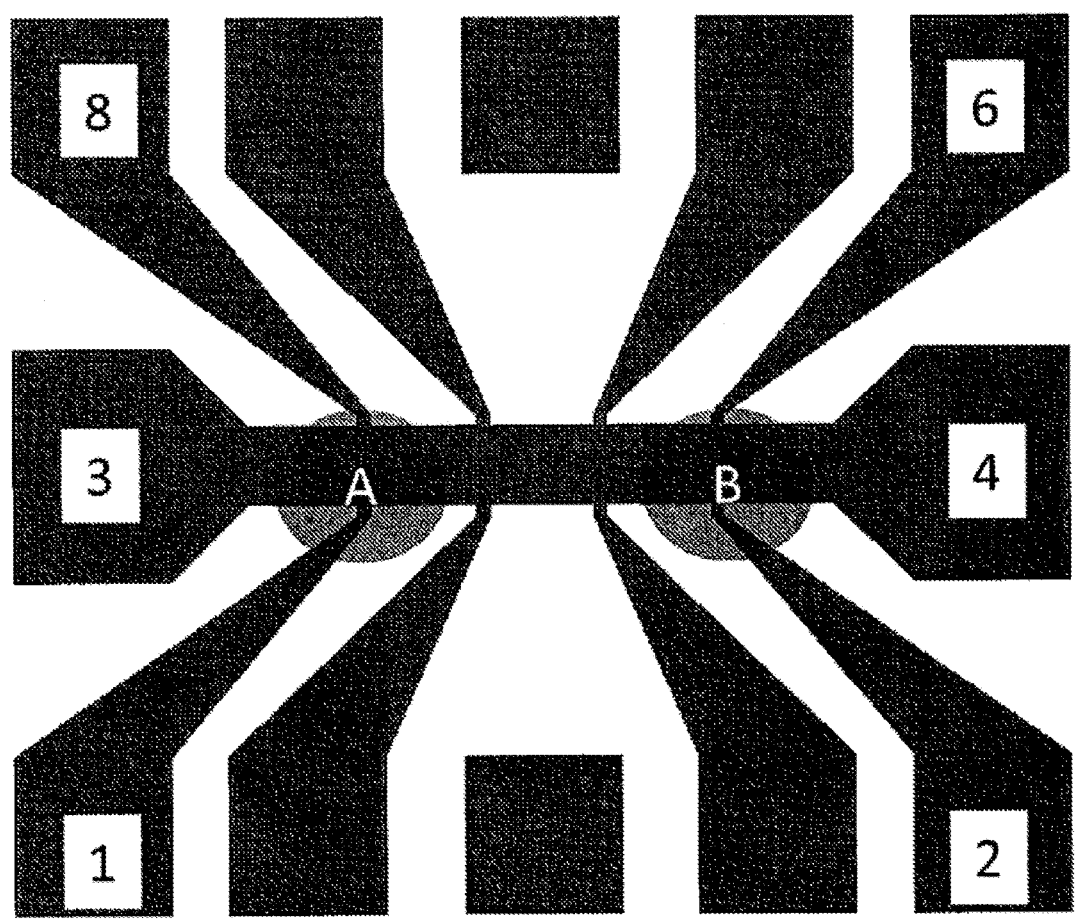
FIG. 1A shows a typical Hall bar device for measuring electron density and mobility of 2DEG. Numbers indicate the locations where electrodes are placed to obtain electronic measurements. Analyte samples are placed in regions A and B (different samples may be placed on each location or the same sample may be applied to each location and the results averaged together).

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Recently, chemical sensors comprising type III-V materials have been developed. In particular, U.S. Pat. No. 7,868,354 (incorporated herein by reference in its entirety) discloses a GaN-based nitric oxide (NO) active sensor, which utilizes, for example, a GaN-based heterostructure field-effect transistors (HFETs), specifically AlGaN—GaN HFETs, with surface functional groups tailored for specificity to NO and S—NO species.

U.S. Patent Application Publication No. 2011/0199102 (incorporated herein by reference in its entirety) discloses a van der Pauw (VDP) sensor comprising an electronic circuit electrically coupled to a surface, the surface comprising a type III-V material, and the electronic circuit measuring a sheet resistivity of the surface using a VDP technique. The VDP sensor may further comprise a macromolecule, such as a porphyrin, an oligonucleotide, a protein, a polymer or a combination thereof in contact with the surface. The VDP sensors may be arranged in an array of similar or different sensors. An electronic circuit electrically coupled to a type III-V material having a two-dimensional electron gas, such as InAs or InN, the electronic circuit measuring an electrical property of the type III-V material having a two-dimensional electron gas. The VDP sensor is useful for detecting a number of chemical species including, but not limited to, NO, $NO_2$, $O_2$, CO, $CO_2$, $SO_2$, $NH_3$, nitrates, nitrites, sulfates, sulfites, and volatile organic materials (VOCs).

U.S. Patent Application Publication No. 2012/0122736 (incorporated herein by reference in its entirety) discloses a sensor comprising an electronic circuit electrically coupled to a type III-V semiconductor material, for example indium arsenide (InAs) and an antibody contacting the type III-V semiconductor material, as well as a method of detecting an antigen using the sensor. The sensor produces measurable changes in the electrical properties of the semiconductor upon antibody-antigen binding events. Electrical properties measurable by the electronic device may include resistivity, capacitance, impedance, and inductance.

Nonetheless, the sensors disclosed in these references do not explore the relation between the surface chemistry (e.g. the oxide composition and oxidation states of the semiconductor material at the surface) and the electronic properties, both of which can be modified upon analyte attachment, or utilize such relation to (1) design new sensor surfaces that respond to various types of analyte molecules with enhanced specificity and sensitivity, (2) detect conformational changes of the analyte molecules upon attachment to the surface, and (3) monitor or control the underlying electrochemical reaction at the semiconductor surface. Accordingly, there is a need for sensors with designed surface characteristics (e.g. a deposited or grown oxide layer) capable of sensing chemical and biological species through the interactions between the analyte molecules and the surfaces of the sensors, as well as controlling the surface-based interactions.

Definitions

The term "type III-V materials" means elements from column III (boron (B), aluminum (Al), Gallium (Ga), Indium (In), Thallium (Tl)) and column V (Nitrogen (N), Phosphorus (P), Arsenic (As), Antimony (Sb), Bismuth (Bi)) of the periodic table of the elements.

The term "two dimensional electron gas" (2DEG) is used to broadly describe electronic structures that are characterized as having a "sea" of electrons that are free to move in two dimensions, but are confined in the third. Such systems are known in semiconductor systems, and have been the basis for breakthroughs in semiconductor physics, such as the quantized Hall effect.

In one aspect, the present invention provides a sensor including: a semiconductor layer having a two dimensional electron gas (2DEG); and an oxide layer in electronic contact with the semiconductor layer.

The sensor of the present invention typically includes a type III-V semiconductor material. Type III-V semiconductors of the present invention include a material selected from the group consisting of boron (B), aluminum (Al), Gallium (Ga), Indium (In), Thallium (Tl), Nitrogen (N), Phosphorus (P), Arsenic (As), Antimony (Sb), Bismuth (Bi), and combinations thereof. For example, suitable semiconductor materials of the present invention include, but need not be limited to, indium arsenide (InAs), indium nitride (InN), gallium arsenide (GaAs), gallium nitride (GaN), aluminum nitride (AlN), aluminum gallium nitride (AlGaN), indium arsenic nitride (InAsN), indium gallium nitride (InGaAs), and combinations thereof. By changing the ratio of the type III material to the type V material, it is possible to engineer a variety of band gap materials, thereby allowing for the construction of devices with desired properties.

Under the proper conditions, type III-V materials possess a two-dimensional electron gas (2DEG). Examples of type III-V materials possessing a 2DEG include, but are not limited to, InAs, InN, AlGaN/GaN heterostructures, and AlGaAs/GaAs heterostructures. For example, InAs and InN based semiconductors possess highly conducting electrons confined to the near surface region. The 2DEG makes these materials extremely sensitive to the presence of surface-adsorbed materials (e.g. biological materials or various chemicals) which change the electrical properties of the 2DEG. Nonetheless, the sensitivity of 2DEG materials to surface-adsorbed materials in relation to the surface chemistry (e.g. the oxide composition and oxidation states of the semiconductor material at the surface) has not been fully appreciated nor used to create sensors.

The semiconductor material is typically supported by a compatible substrate. In one embodiment, the sensor of the present invention includes an InAs semiconductor layer grown by molecular beam epitaxy (MBE) directly on GaAs substrates. The thickness of the semiconductor layer is typically from about 10 nm to about 1000, preferably from about 20 nm to about 500 nm, more preferably from about 50 nm to about 200 nm.

The oxide layer of the present invention is in electronic contact with the semiconductor layer. For example, the semiconductor material of the present invention may be terminated with an oxide layer which acts as a sacrificial reactant in a surface-based chemical reaction. Such surface-based chemical reactions can be used to detect an analyte molecule.

In one embodiment, the oxide layer is a native oxide layer formed by oxidation of the same semiconductor material. Typically, the semiconductor is prepared and exposed to atmosphere in a controlled manner for the native oxide layer to form. For example, the native oxide can be formed by exposing a InAs surface to atmosphere under various predetermined conditions (such as temperature and duration).

Alternatively, the oxide layer can be a deposited/grown oxide layer, which is formed by depositing or growing a layer of oxide of a material that is the same as, or different from, the semiconductor material of the sensor. The oxide can be an oxide of a material selected from the group consisting of boron (B), aluminum (Al), Gallium (Ga), Indium (In), Thallium (Tl), Nitrogen (N), Phosphorus (P), Arsenic (As), Antimony (Sb), Bismuth (Bi), and combinations thereof. In addition, oxide of transition metals (such as Titanium (Ti), Zirconium (Zr), Hafnium (Hf)) or non-metal elements (such as Silicon (Si)) or any combinations thereof can also be used. Suitable oxide layer include, for example, indium oxide, arsenic oxide, and combinations thereof. The oxide can include a uniform oxidation state (e.g. $As_2O_3$ or $In_2O_3$) or a mixture of various oxidation states (e.g. $As_2O_3$, $As_2O_5$, and $InAsO_4$). Examples of suitable oxide also include oxides of In and As ($In_xAs_yO_z$), $Hf_xO_y$, $Al_xO_y$, $Si_xO_y$, $Hf_xAl_yO_z$ or $Hf_xSi_yO_zN_q$ (x, y, z, and q in each formula indicate the average of various oxidation states in the oxide layer), or any combinations thereof.

Oxides can be deposited or grown using standard techniques, such as molecular beam epitaxy (MBE), atomic layer deposition (ALD), thermal and/or plasma treatment in an oxidizing atmosphere, or in solution. Prior to preparation of a non-native oxide layer using one of the standard processes, the native oxide is completely or partially removed and the new oxide is deposited or grown. The degree to which the native oxide can be removed and the specific physical/chemical mechanism used will lead to defects that modify the 2DEG density and mobility.

In one embodiment, the oxide layer is engineered by first terminating a "clean" InAs surface with a layer of a type III or type V material, which includes one or more monolayers (ML). For example, the oxide layer can be grown on the InAs surface under vacuum conditions. Alternatively, the InAs surface is deoxidized under vacuum through heating to approximately 450° C. under an $As_2$ or $As_4$ flux and is then terminated by the type III or type V material layer. Upon exposure to atmosphere, an oxide layer will form on the terminating layer (i.e. the type III or type V material layer). Since the terminating layer has different chemical and physical properties from the InAs surface, the oxidation process (i.e. interactions of the surface material with oxygen) will produce different oxide layers. In particular, the chemical composition of oxide layer formed on the terminating layer will differ from that formed on the non-terminated InAs surface.

Suitably, the properties of the oxide layer is engineered by controlling the chemistry of terminating layer. For example, the thickness of the oxide layer can be modified by the material in the terminating layer. The thickness of the oxide layer is typically from about 0.1 nm to about 10 nm, preferably from about 0.2 nm to about 5 nm, more preferably from about 0.2 nm to about 1 nm.

In addition, the oxidation state of the oxide layer may also be adjusted by controlling the material and processing of the terminating layer. For example, a particular composition of the oxide layer (e.g. having a particular oxygen-rich species, such as $InAsO_4$, at a certain level) can be achieved by applying a suitable terminating layer. Different oxide compositions that are, for example, rich in In-oxide components such as $In_2O_3$ or In—OH, or rich in either $As_2O_3$ or $As_2O_5$, can be synthesized through appropriate process conditions. In addition, oxides containing transition metals (such as Titanium (Ti), Zirconium (Zr), Hafnium (Hf)) or non-metal elements (such as Silicon (Si)) can also be prepared. The oxide composition will determine the interaction between the target analyte and the oxide layer, based on the key ligands present in the analyte molecules, which have differential interactions with various oxide phases. For example, the phosphate backbone of DNA binds much more readily to In oxides compared to As oxide, while amine groups bind to both As oxide and In oxide to a similar extent. These binding differences will determine both the conformation of the attached analyte and the modifications in the oxide composition resulting from the attachment. The oxide modifications include chemical reactions between the analyte and components of the oxide layer. As a result of these chemical reactions, defects are created such as vacancies and interstitial Group III and V elements, which in turn modify the electron density and mobility of the 2DEG of the semiconductor material; these changes in the 2DEG are then sensed as described herein to detect interaction of analytes with the sensor surface/oxide layer.

The oxide layer can be further engineered for sensing applications. The chemical composition and defect concentrations of the oxide layer affect the surface-based ligand interaction and analyte attachment. For example, a ligand or analyte can interact with the oxide and etches the oxides at an etching rate that is dependent upon the oxide composition. That is, different oxide layer will react differently, at different rate, to the etching effect caused by ligand or analyte interaction. For example, we have found that the carboxylic acid group (e.g. those in DNA molecules) preferentially etches (or causes the dissolution of) the As oxide component of the In oxide/As oxide formed on InAs surface. Thus, oxide layer with varying composition as a function of depth (from the semiconductor interface to the surface of the oxide) may be prepared. The oxide can be grown in a layered fashion or by grading the composition with a wide range of gradient types (for example, linear grading, parabolic grading, etc., depending on the fabrication method). When the oxide layer includes two or more non-oxygen elements (A and B, such as In and As), the oxide ($A_xB_yO_z$, representing the average oxidation states of all oxides) may have a varying composition (defined by x, y, and z) depending on the depth of the oxide layer. Such depth-dependent variation in composition, combined with the concentration of A, B, O defects (specifically interstitials, vacancies, and antisite defects) will determine the ligand-interaction and the ligand-enhanced oxide dissolution rates.

Oxides can also be patterned by lithography and then etched. Alternatively, the semiconductor material can be patterned and etched prior to the formation of an oxide layer. The oxide layer can be created with lateral variations in composition and/or defect concentration. This will lead to lateral variations in ligand-interaction and analyte attachment. The sensor of the present invention may be configured in arrays in order to simultaneously measure different samples. Each array element is an individual sensor surface or a region of a sensor surface with specific oxide properties (such as composition and thickness). By electronically interrogating each array element, sensors with varying sensitivities to analyte interactions at each element can be constructed.

It is contemplated by the present invention that the oxide layer, as a sacrificial reactant layer in a surface-based chemical reaction, can be customized to respond to various analytes, in various forms of samples (gaseous or liquid), and at various analyte concentrations with improved sensitivity, specificity, and dynamic range. Suitably, the oxide layer can be designed and utilized as a a) multiphase native oxide of variable thickness;
b) deposited oxide of controlled phases and thickness;
c) patterned oxides designed to produce spatial variations in chemical reactions and rates; or
d) layered oxide with layers designed to be consumed during reactions revealing a new reactant layer to achieve dynamic control during surface chemical reactions. Upon consumption of a specific oxide layer, a chemical switch is achieved with a concurrent electronic signal change which can be measured.

Typically, upon contact with an analyte molecule, the oxide layer of the present invention undergoes a surface-based chemical reaction in which the oxide layer is sacrificed, thereby causing a change in the electrical properties of the 2DEG of the semiconductor material. Such electrical properties include, but are not limited to, electron density and mobility. These electrical properties are different when the device is illuminated (light conditions) and when the device is not illuminated (dark condition). By comparing the electron density and mobility measured under light and dark conditions, additional information on surface chemical reactions is obtained.

Accordingly, the sensor of the present invention may further comprise an electronic circuit capable of measuring the electrical properties of the 2DEG of the semiconductor material. For example, determination of the electron density and mobility in the 2DEG may be carried out by performing Hall effect measurements using a Hall bar device as discussed further below. Methods of measuring the Hall effect using a standard Hall bar device are within the knowledge of a skilled person in the art. Other electrical properties of the semiconductor material can also be measured. Such properties may include, but are not limited to, resistivity, conductivity, inductance, impedance, and capacitance. For example, the resistivity of a semiconductor material and materials functionalized to the semiconductor material may be measured by attaching four contacts to the portion of type III-V semiconductor material and monitoring the electrical potential between two contacts as a steady current is fed between the remaining two contacts. Other methods of measuring resistivity (or conductance) may also be used.

The oxide layer of the present invention can be modified with a functionalizing molecule. The functionalizing molecule is capable of being adsorbed by the surface of the oxide layer to form a layer of chemical probes. A functionalized surface is formed upon the adsorption of one or more functionalizing molecule (i.e. probe) thereto. It is contemplated by the present invention that the customization and attachment of the functionalizing molecules will improve the sensitivity and analyte specificity of the sensor of the present inventor in the detection of various types of analyte molecule. For example, the functionalizing molecule can undergo a specific interaction (such as affinity binding) with the analyte molecule to improve the selective and sensitivity of the sensor to such analyte molecule. The specific interaction between the analyte molecule and the surface of the sensor (with or without the functionalizing molecule) may result from the presence of a functional group on the analyte molecule, including carboxyl group (—$COO^-$), phosphoryl group (—$OPO_3^{2-}$), amino group (—$NH_2$), amide group (—NH—CO—), and thiol group (—SH), etc. In addition, the interactions between the analyte molecule and the sensor surface may result from any ionic, non-ionic, and hydrogen-bonding interactions. The ionic interactions include the attraction between ions or molecules with opposite electric charges. The non-ionic interactions include covalent interaction (such as formation of covalent bonds), van der waals interaction (such as dipole-dipole interactions), π-π interactions, and hydrophobic effect between non-polar molecules.

Suitable functionalizing molecules include, but are not limited to, biological materials such as oligonucleotides, peptides/polypeptides, proteins, and combinations thereof. Other functionalizing molecules can include polymers, including naturally-occurring and synthetic polymers. Examples of oligonucleotides include, but are not limited to, polymers of nucleic acids containing the bases cytosine, guanine, adenine, thymine, and uracil. Examples of proteins include antibodies, ligands, hormones, cytokines, growth factors, receptors, receptor ligands. Examples of polymers may include, but are not be limited to, homopolymers, co-polymers, and block co-polymers comprising known monomer units, such as ethylenes, styrenes, vinyl chlorides, acrylics, urethanes, methacrylates, isobutalenes, haloethylenes, and lactones.

The sensors of the present invention can be adapted to detect and measure a wide variety of chemical and biological analytes contained in various fluids (air, water, blood, waste effluent, saliva, urine, etc.). Such sensors can be used in, for example, medical diagnostics, emissions control, and environmental monitoring, among other applications. In one embodiment, the oxide layer of the sensor is modified with an oligonucleotide to detect one or more DNA molecules in a fluid.

In another aspect, the present invention provides a method detecting an analyte molecule, the method comprising:

providing a sensor comprising (a) a semiconductor layer having a two dimensional electron gas (2DEG), and (b) an oxide layer in electronic contact with the semiconductor layer;

making a first measurement of an electrical property of the 2DEG;

contacting the analyte molecule with the oxide layer of the sensor;

subsequently making a second measurement of the electrical property of the 2DEG;

wherein the difference between the first and second measurement of electrical property of the 2DEG indicates the presence of the analyte molecule.

Figure 8:
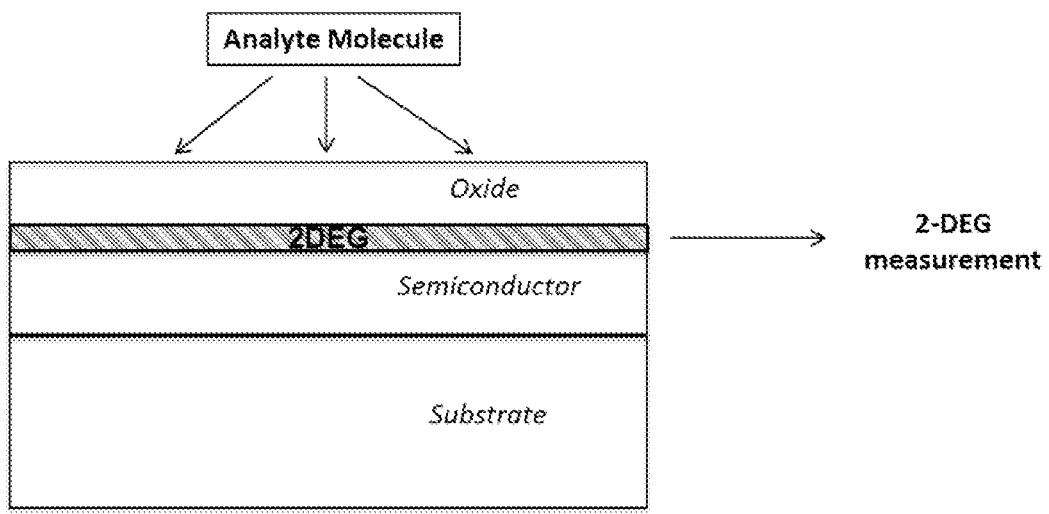
FIG. 8 shows a non-limiting exemplary illustration of the sensing process involving an oxide layer on the sensor's surface.

FIG. 8 shows a non-limiting exemplary illustration of the sensing process involving an oxide layer on the sensor's surface. Without being limited to a particular theory, it is hypothesized that, upon contacting an analyte molecule, chemical electronic coupling occurs between the analyte molecule and the sensor's surface through charge transfer through the oxide layer of the sensor and modification of the interfacial electronic states. Accordingly, there is a quantitative correlation between the surface chemistry (such as oxide composition) and the electrical properties (such as electron density and mobility) in the 2DEG of the semiconductor material. The electrical properties can be measured, for example, by measuring the Hall effect using devices and processes known in the art. In one embodiment, the electrical properties of the 2DEG are measured under illuminated (light) and dark conditions, and the results are compared. Suitably, each of the first measurement of the electrical property of the 2DEG and the second measurement of the electrical property of the 2DEG is made by comparing a measurement of the electrical property under light conditions to a measurement of the electrical property under dark conditions. For example, four independent measurements (light electron density, dark electron density, light mobility, dark mobility), as opposed to two independent measurements (electron density and mobility under either dark or light conditions) can be used to determine reaction products, such as free As, resulting from the chemical interactions between the analyte and oxide layer. The use of independent measurements under light and dark conditions can reduce noise intrinsic to the measurement hardware, software for data analysis, measurement electronics comprising a circuit, and device imperfections.

The composition and other chemical and physical properties of the oxide layer can by characterized by methods known in the art. For example, the percentage of a particular oxide as a part of the oxide layer, as well as the ratio of the abundance of two different elements of the surface (e.g. N vs. In, or P vs. In) can be determined by X-ray photoelectron spectroscopy (XPS) measurement.

It is also contemplated by the present invention that the concentration of an analyte molecule can be measured based on a specific interaction between the analyte molecule and a functionalizing molecule attached to the sensor surface. Such interactions may result from the presence of a functional group on the analyte molecule, such as carboxyl group (—COO⁻), phosphoryl group ($—OPO_3^{2-}$), amino group (—NH$_2$), amide group (—NH—CO—), and thiol group (—SH). In addition, the interactions between the analyte molecule and the sensor surface may result from any ionic, non-ionic, and hydrogen-bonding interactions.

In one embodiment, the method of the present invention comprises providing a sensor with an oxide layer conditioned with a functionalizing molecule, such as oligonucleotide, peptide, polypeptide, protein, polymer, and combinations thereof. The functionalized surface will have an improved specificity and sensitivity for a particular analyte molecule. For example, an oligonucleotide may be attached to the sensor surface as a probe, and the sensor functionalized with the oligonucleotide probe can be used to determine the concentration of a DNA molecule that has a nucleotide sequence partially or completely complimentary to the sequence of the probe molecule. The detection of complementary DNA in the sample is enhanced due to the affinity binding between the complementary DNA and the probe DNA on the sensor surface. In contrast, the sensor does not respond to non-complementary DNA molecules (or "junk DNA") with the same level of sensitivity since they cannot bind to the probe DNA with affinity. Accordingly, and the sensor with probe DNA will detect complementary DNA molecules with improved selectivity and sensitivity.

In one embodiment, the molecule of the surface-based chemical reaction that can be sensed by the present invention is a biomolecule, such as DNA, RNA, protein, or lipid. Suitably, the biomolecule is a DNA molecule.

The method of the present invention also comprises measuring a chemical or biological analytes contained in various fluids (air, water, blood, waste effluent, saliva, urine, etc.). In one embodiment, the method comprises measuring the concentration of a biomolecule (such as DNA) in an aqueous solution.

Such sensors can be used in, for example, medical diagnostics, emissions control, and environmental monitoring, among other applications. Additionally, the sensors may be configured in arrays in order to simultaneously measure different samples.

The determination of the concentration of the analyte molecule may be carried out based on the quantitative change of an electrical property of the 2DEG of the semiconductor material in relation to the concentration of the molecular species being analyzed. For example, the sensor can be calibrated with samples containing known concentrations of the analyte molecule to generate a standard curve, from which the concentration of the analyte in an unknown sample can be determined by comparing the sensor's response to the unknown sample to the standard curve. Such data analysis process is within the knowledge of a skilled person in the art.

The examples below are not intended to limit the scope of the invention in any way, but are provided to illustrate the principles of the invention and to demonstrate the capability of the sensors of the invention.

EXAMPLES

Example 1. Biosensing Application

Undoped InAs films with thicknesses from 50-200 nm were grown by molecular beam epitaxy (MBE) directly on GaAs substrates. The residual (non-2DEG) background electron concentration in the InAs was assumed to be in the low $10^{16}$-mid $10^{17}$ cm$^{-3}$ range. The measured electron concentration and mobility, determined using Hall measurements included the parallel conductance of the 2DEG, the non-accumulated background electron concentration in the InAs, and a parasitic electron accumulation layer resulting from defects at the InAs—GaAs substrate interface.

An oxide layer including the oxides of In and the oxides of As was formed by exposure of the InAs surface to air. As a second method, oxides of In and oxides of As were formed by terminating the surface before air exposure with a monolayer of In or by a monolayer or more of As. The air-exposed oxides were a mixture of $In_2O_3$, In—OH, $As_2O_3$, and $As_2O_5$. The oxide layer typically had a thickness of about 3 nm, and was rich in As-oxide at the oxide surface. Oxide layers produced by the second method were of the same approximate thickness but were thinner and less oxygen-rich when using an In termination in comparison to an As termination. The As termination also results in more $As_2O_5$. The composition of the oxide determines which analyte ligands preferentially bind to the surface. For example, higher oxidation state As oxides, such as $As_2O_5$ have a negative charge in aqueous near-neutral pH and therefore produce an electrostatic repulsion to negatively charged ligands of the analyte. On the other hand, hydroxylated In oxide-rich surfaces have a positive charge in aqueous near-neutral pH solutions and are attractive to negatively-charge ligands of the analyte. In addition, to tuning electrostatic interactions, acid-base reactions can be tuned by tuning the overall acidity or basicity of the surface through modifying the composition.

The adsorption of 5'-carboxylic-acid-modified DNA oligomers (5'-/5CarBxT/CT CAC CAT AAT TCT GGA ACC ACC T-3') onto InAs surfaces were used as probes (i.e. the transduction depends on hybridization of the target DNA in solution to the surface-attached probe). The InAs surfaces were cleaned and then exposed to the oligonucleotides at fM to µM concentrations in 24 mL of $H_2O$ for 24 hours under conditions minimizing light exposure. After incubation, the samples were rinsed with water and dried (five times) with ultra-high purity $N_2$. Hall bar devices were fabricated with TiAu metallization and mounted onto a PCB board.

For the sensing test, two InAs surface samples were used. One sample functionalized with the probes described above (µM functionalization) was exposed to complementary target DNA of varying concentration in water for 30 minutes. In comparison, the other sample was exposed to junk DNA (i.e. non-complementary to the sequence of the probe DNA as described above). The difference in the electron density and mobility in the InAs surfaces before and after the exposure to DNA molecules (target DNA vs. junk DNA) were recorded using a standard Hall bar measurement method (as shown in FIG. 1A), and the results were compared between the surface exposed to target DNA and the surface exposed to junk DNA).

Figure 1B:
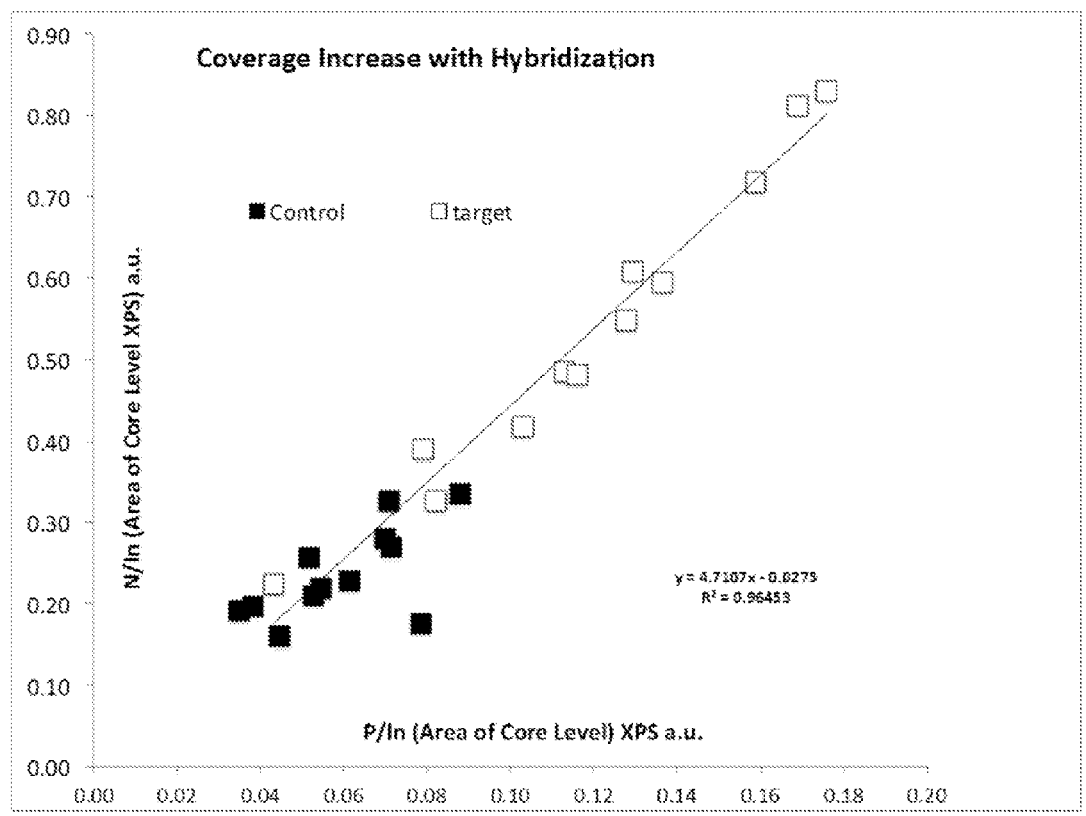
FIG. 1B shows X-ray photoelectron spectroscopy (XPS) data showing the relative concentrations of nitrogen (N/In) and phosphorus (P/In) on InAs surfaces exposed first to a single-stranded DNA molecule (which is attached as a probe) and then to either a complementary DNA target which hybridizes with the surface-attached single-stranded probe DNA (open squares) or to a junk DNA (filled squares). The Y axis shows the XPS-derived core level area ratio of N (nitrogen)/In (indium), which is directly related to the abundance of N at the surface; and the X axis shows the core level area ratio of P (phosphorus)/In (indium), which is directly related to the abundance of P at the surface.

As shown in FIG. 1B, the final DNA surface concentration (i.e. the density of DNA molecules bound to the surface), as measured by the relative concentrations of nitrogen and phosphorus on the surface, was much higher on the InAs surface exposed to complementary target DNA after hybridization, compared to the InAs surface exposed to the non-complementary, junk DNA, where only non-specific surface interactions took place.

Thus, the difference in in the electron density and mobility in the InAs surfaces depends on the DNA coverage and binding and the related changes in the InAs oxide resulting from the DNA-oxide chemical interactions. The affinity binding interactions between the probe DNA and the complimentary DNA modify the oxide chemistry on the sensor surface and are strongly coupled to the electron density and mobility of the 2DEG in the semiconductor material. Thus, measuring the 2DEG density and mobility before, after, and during the binding reactions provides information on the molecular coverage and the molecular binding (and conformation).

Figure 2:
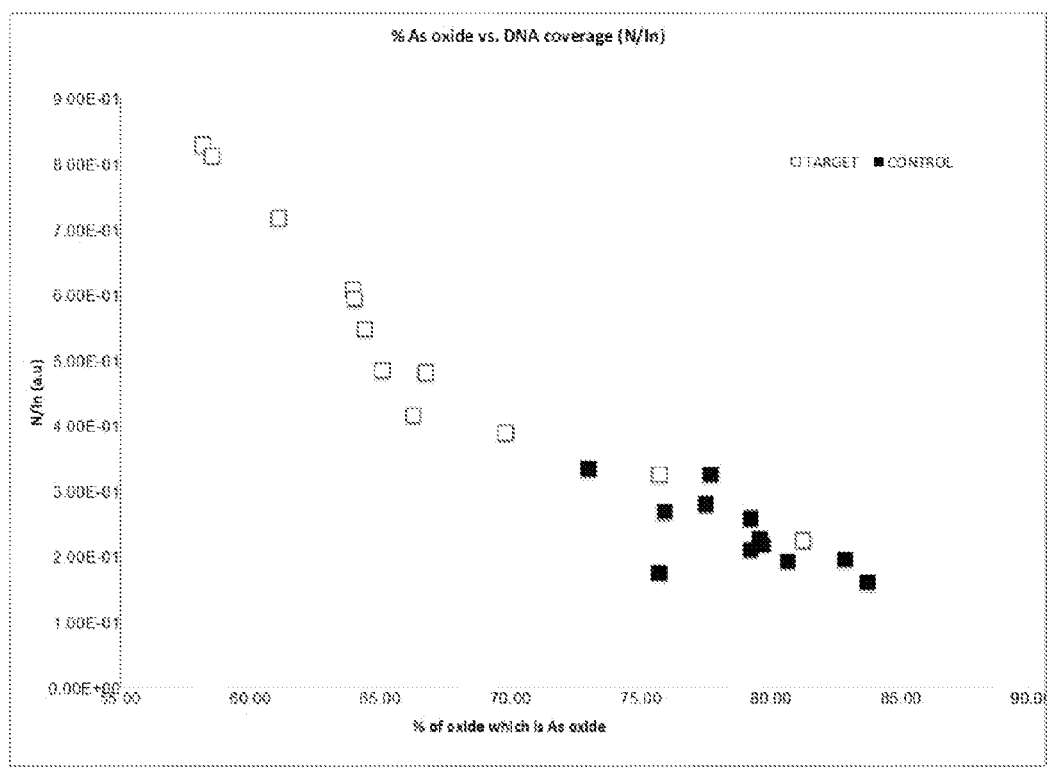
FIG. 2 shows X-ray photoelectron spectroscopy (XPS) data showing that the In oxide component of the native oxide (which is a mixture of In oxides and As oxides) is enhanced as a result of the hybridization reaction and higher DNA surface attachment (Target). The X axis is the percentage of As oxide for control and target surfaces (as determined from XPS core level deconvolution); the Y axis is the relative DNA coverage on the surface as determined from XPS by using the N/In core level area ratio (same quantity as the Y axis of FIG. 1).

The results suggest that the chemical electronic coupling occurs through charge transfer through the oxide and modification of interfacial electronic states. FIG. 2 shows that the In oxide component of the native oxide (which is a mixture of In oxides and As oxides) on the InAs surface is enhanced as a result of the hybridization reaction (compared to the non-specific surface interaction) and higher DNA surface attachment. This shows that the chemistry of the oxide is modified through DNA surface attachment and associated chemical interactions (e.g. by the selective reduction, or "sacrifice," of a particular oxide).

Figure 3:
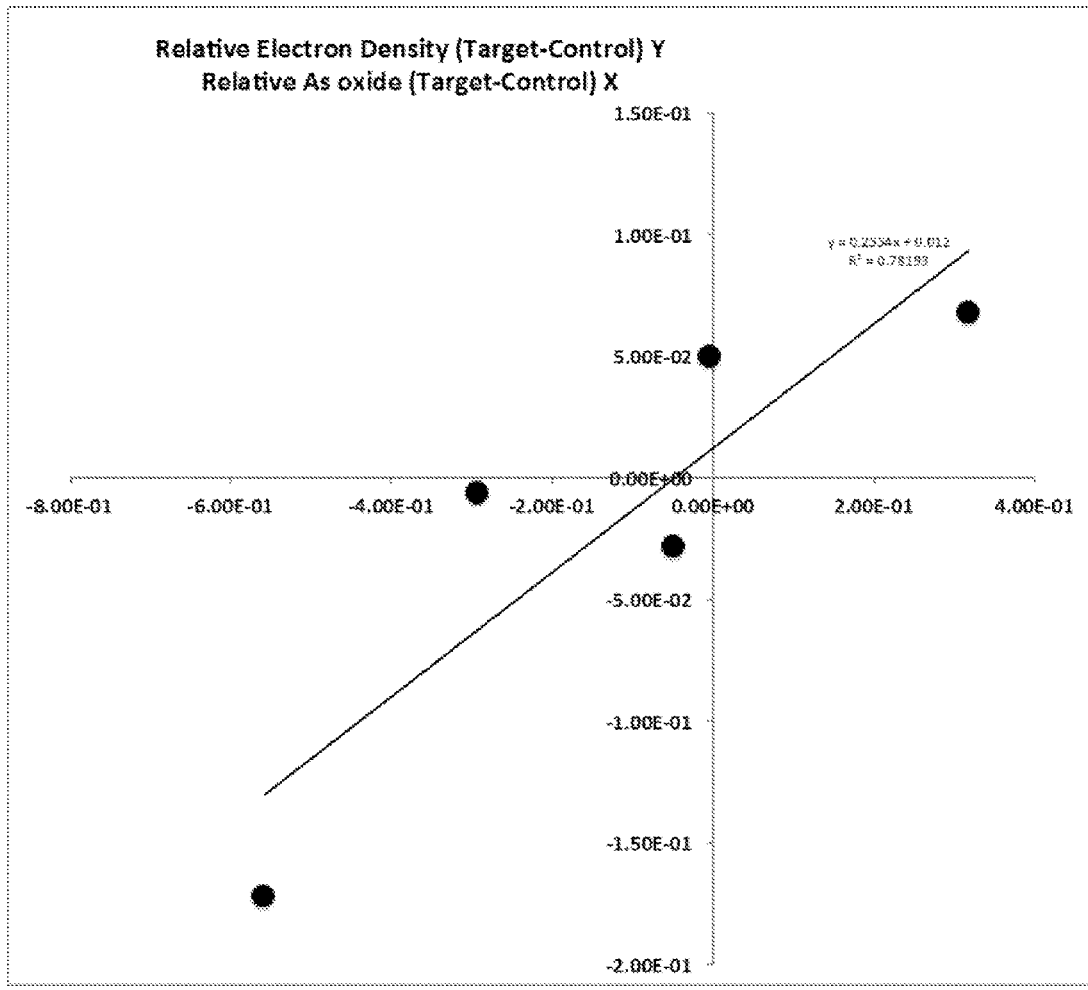
FIG. 3 shows the difference (normalized) in electron density of the 2DEG on the InAs surface between the hybridized DNA exposure and control, in relation to the difference in the oxide composition. The Y axis shows the difference (in relative values) in electron density (Hall effect measurement) between the surface exposed to complementary DNA which then hybridizes and the control surface (Target-Control); the X axis shows the difference (in relative values) in As oxide percentage in a mixed In oxide/As oxide native oxide layer (XPS determination) between the surface exposed to complementary DNA and the control surface (Target-Control).

Further, as shown in FIG. 3, the difference (normalized) in electron density (Hall effect measurements) of the 2DEG between the hybridized DNA exposure and control (Target-Control) is directly related to the difference in the oxide composition (measured as a change in the relative amounts of As oxide in the mixed In oxide/As oxide native oxide). Thus, there is a measurable correlation between the surface chemistry (oxide composition) and the electron density and mobility of the 2DEG on the surface of a semiconductor material (e.g. InAs surface).

The specific chemical interactions between the As and In oxide components and the DNA functional groups (phosphate backbone, nitrogen in the bases, and carbon groups) drive the specific attachment dominance in the DNA overlayer and the changes in the average conformation of the DNA molecule attached to the surface. For example, when phosphate backbone binding is dominant (i.e. binding to the surface through the phosphate group on the DNA backbone), surface adsorbed DNA is, on average, in a more horizontal, or lying down, position.

To study the correlation between the oxide surface chemistry and the conformation of the attached DNA molecules, the 2DEG density upon adsorption of single-stranded DNA on the InAs surface was measured. The 5'-carboxylic-acid-modified DNA oligomers (5'-/5CarBxT/CT CAC CAT AAT TCT GGA ACC ACC T-3') were allowed to be adsorbed onto the InAs surfaces. The InAs surfaces were cleaned and then exposed to the oligonucleotides at micromolar (µM) concentrations in 24 mL of $H_2O$ for 24 hours under conditions minimizing light exposure. After incubation, the samples were rinsed with water and dried (five times) with ultra-high purity $N_2$. Hall bar devices were fabricated with TiAu metallization and mounted onto a PCB board.

Figure 4:
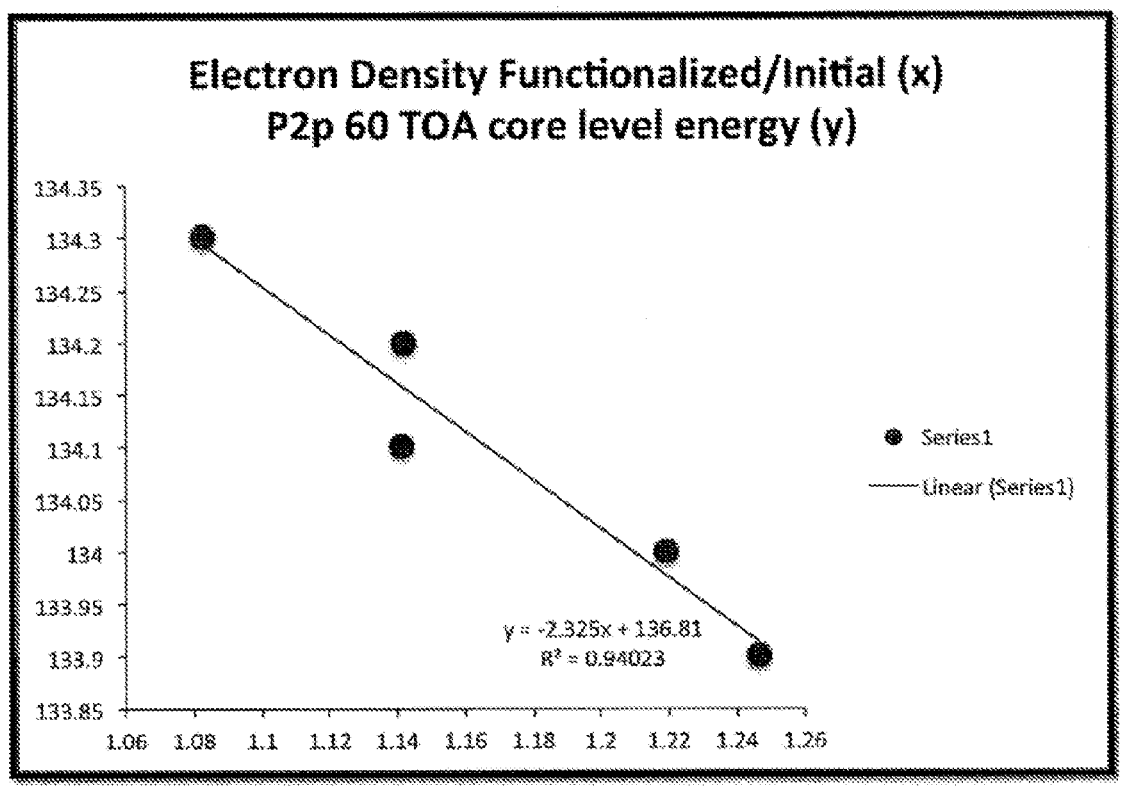
FIG. 4 shows the normalized 2DEG density change upon adsorption of single-stranded DNA. The Y axis is the energy of P 2p core level (phosphorus) measured using XPS; the X-axis is the ratio of the density of the 2DEG (Hall effect measurement) of the surface exposed to the single-stranded DNA to that of the surface not exposed to the single-stranded DNA.

As shown in FIG. 4, the core level (Y axis, measured by XPS) shifts to higher energy when the electron density (X axis, measured by Hall effect) around it changes from an electron rich state (higher ratio on X axis) to a more positively charged state (low ratio on X axis) after the binding of the single-stranded DNA. This represents a change in the phosphate backbone binding to the oxide layer, which results in a direct change in the 2DEG.

Thus, the normalized 2DEG density increased upon adsorption of single-stranded DNA, as more phosphate bonds were made to the In-oxide component of the surface oxide, as determined by the shift in the P 2p core-level binding energy measured with XPS. This indicates that the density of the 2DEG increases as phosphate backbone binding (and horizontal conformation of the adsorbed DNA) become dominant.

Figure 5:
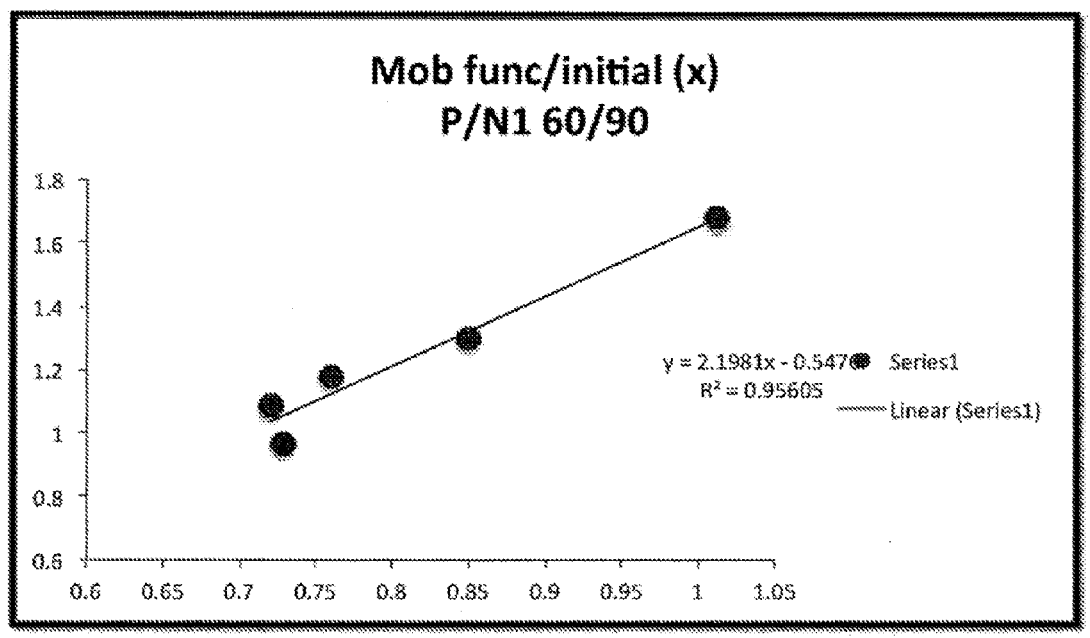
FIG. 5 shows the normalized change in mobility after attachment of DNA to the surface in relation to the average molecular conformation. The Y axis is the ratio of the density of the 2DEG (Hall effect measurement) of the surface exposed to the single-stranded DNA to that of the surface not exposed to the single-stranded DNA; the X axis is the ratio of the P 2p core level area/N1 (the lower energy peak fit of the N1s core level) measured at a 60 degree take-off angle (a more shallow probe of the surface) to the 90 degree take off angle (deeper penetration of the measurement).

The 2DEG density and mobility have an inverse power law relationship but the strength of this relationship (power) is modified in relation to DNA coverage and average molecular conformation. FIG. 5 shows that, as the DNA becomes more upright (on average in the molecular overlayer), the electron mobility change (x-axis, normalized) increases. The average conformation is determined using the change in P/N abundance as a function of take-off angle, so the ratio indicates that P is more abundant at the surface of the molecular overlayer in comparison to that at the molecular overlayer-oxide interface. For example, the X axis of FIG. 5 is the ratio of the P 2p core level area/N1 (the lower energy peak fit of the N1s core level) measured at a 60 degree take-off angle (a more shallow probe of the surface) to the 90 degree take off angle (deeper penetration of the measurement). This ratio increases, indicating that the relative abundance of P to N1 is increasing at the surface of the molecular overlayer (on average) and therefore the average conformation of the DNA is changing and can be measured electrically through the 2DEG mobility.

Figure 6:
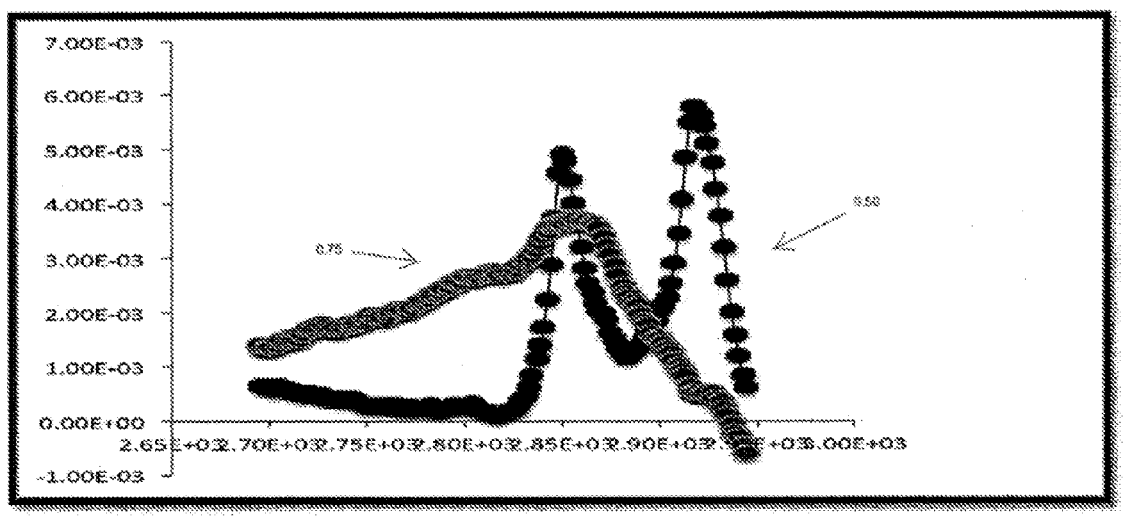
FIG. 6 shows that the conformation assessment using the XPS ratio as shown in FIG. 5 is confirmed by the change in the FTIR spectrum of the DNA overlayer. The Y axis is intensity of the IR vibrations; the X axis is the wavenumber for the vibrations (used as a fingerprint for vibrations of known functional groups). The change in the FTIR spectrum is associated with a more ordered DNA layer as evidenced by the appearance of the sharp methylene vibrations at 2850 and 2917 $cm^{-1}$. The ordered single-stranded DNA layer is associated with a large P/N1 60/90 value, while the disordered DNA layer is associated with a low value of P/N1 60/90.

The conformation change indicated by FIG. 5 is confirmed using Fourier Transform IR spectroscopy (FTIR) data as shown in FIG. 6, which shows that the 2DEG density is approximately 25% lower when the DNA has less P attachment (i.e. binding through the phosphate group) to the InAs surface, but more hydrogen bonding and an ordered overlayer (marked as "0.5," for sample exposed to 0.5 µM DNA). The change in the spectrum is given for two samples with the largest electron density change after functionalization. These data correspond to vibrations of the methylene groups in the DNA, and show the comparison between a more ordered (marked as "0.5") and a more random conformation (marked as "0.75," for sample exposed to 0.75 µM DNA). These results again show that the average conformation is changing (as the chemistry of the oxide layer changes), leading to a change in the 2DEG density and mobility.

Figure 7:
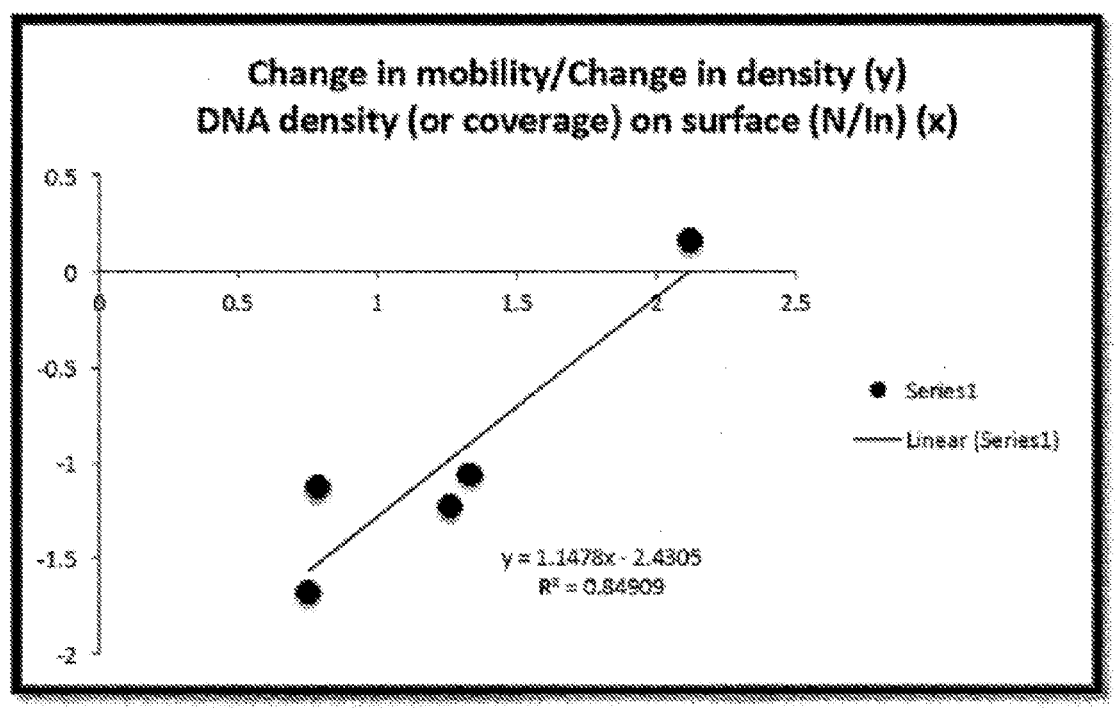
FIG. 7 shows the ratio of mobility to density in relation to the DNA overlayer relative coverage as determined using the relative abundance of nitrogen (in DNA) to In in the oxide and semiconductor. The Y axis is the change in mobility (expressed as the ratio of the density of the 2DEG (Hall effect measurement) of the surface exposed to the single-stranded DNA to that of the surface not exposed to the single-stranded DNA). The X axis is the DNA coverage expressed as the ratio of N/In (XPS measurement).

Further, FIG. 7 shows that as the DNA coverage increases the ratio of mobility to electron density increases (as determined using the relative abundance of nitrogen (in DNA) to In in the oxide and semiconductor). Therefore, the ratio of mobility to electron density of the 2DEG of the semiconductor material can be used to determine molecular overlayer coverage upon attachment of such molecules (e.g. DNA) to the surface.

Figure 9A:
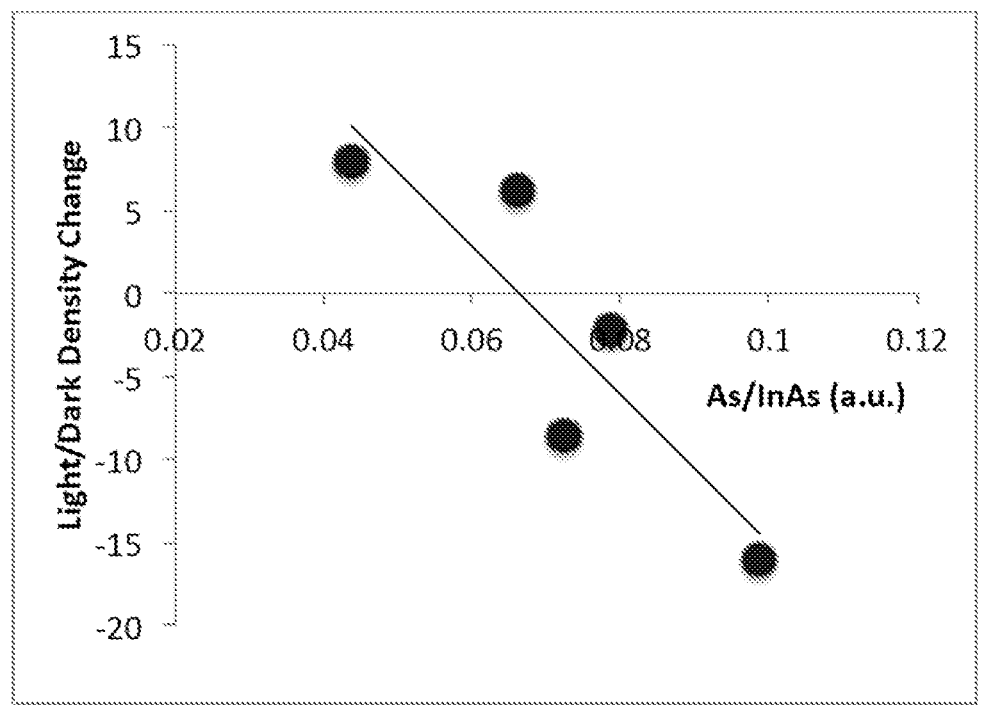
FIG. 9A shows difference between the density measured by XPS under light condition and that measured under dark condition (Y axis) in relation to the concentration of free As in the InAs semiconductor measured by XPS (As/InAs, X axis)
Figure 9B:
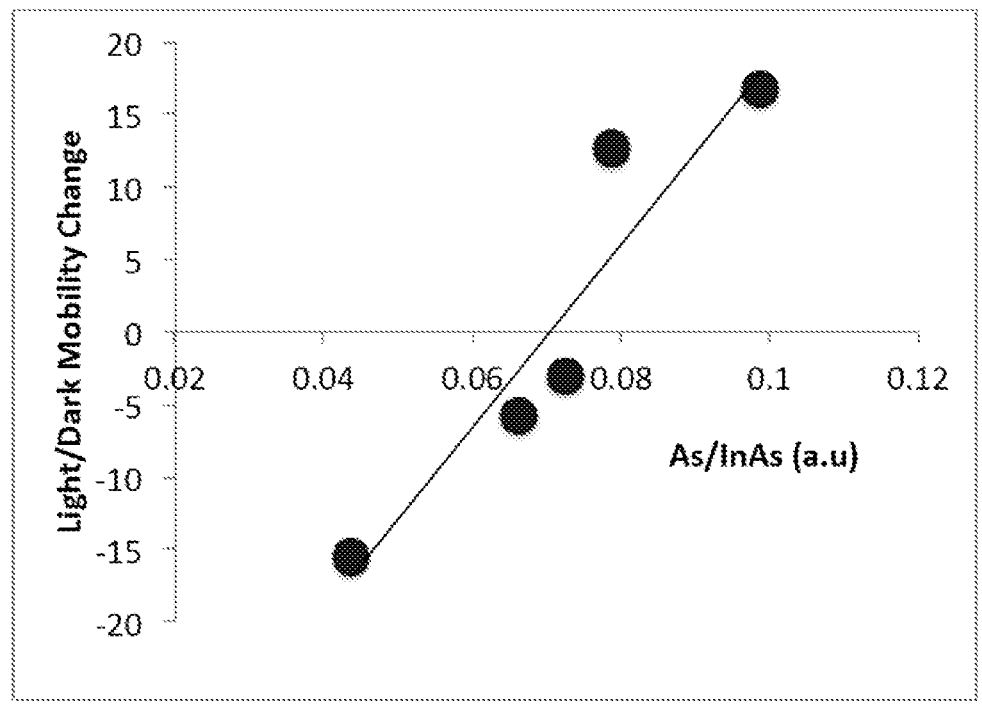
FIG. 9B shows difference between the mobility (Hall effect measurements) under light condition and that measured under dark condition (Y axis) in relation to the concentration of free As in the InAs semiconductor (As/InAs, X axis).

Further, the state of free As (i.e., the As atoms not bound to oxygen or to In in the InAs semiconductor) was measured using XPS. Without being limited to a particular theory, it is hypothesized that free As is a key product of As oxide reduction resulting from As oxide-ligand interactions. In particular, it is hypothesized that the reduction of As oxide occurs when DNA molecules attach to the oxide layers, and the rate of the reduction of As oxide increases with increasing exposure to DNA molecules. Free As concentration was determined by carrying out Hall measurements under light conditions (in ambient room light) and under dark conditions (in which the experiment device was covered and blocked from any source of light) and comparing the electron density and mobility measurements under both of these conditions, as shown in FIGS. 9A and 9B. By comparing the measurement of both electron density and mobility under light and dark conditions, using a ratio, for example, four independent measurements (light electron density, dark electron density, light mobility, dark mobility), as opposed to two independent measurements (electron density and mobility under either dark or light conditions) were used to determine reaction products, such as free As, resulting from the chemical interactions between the analyte and oxide layer. The use of four independent measurements reduces noise intrinsic to the measurement hardware, software for data analysis, measurement electronics comprising a circuit, and device imperfections. We hypothesize that the differences in density and mobility arise from the intrinsic nature of the reaction-product defects and their response to illumination by light.

Figure 10:
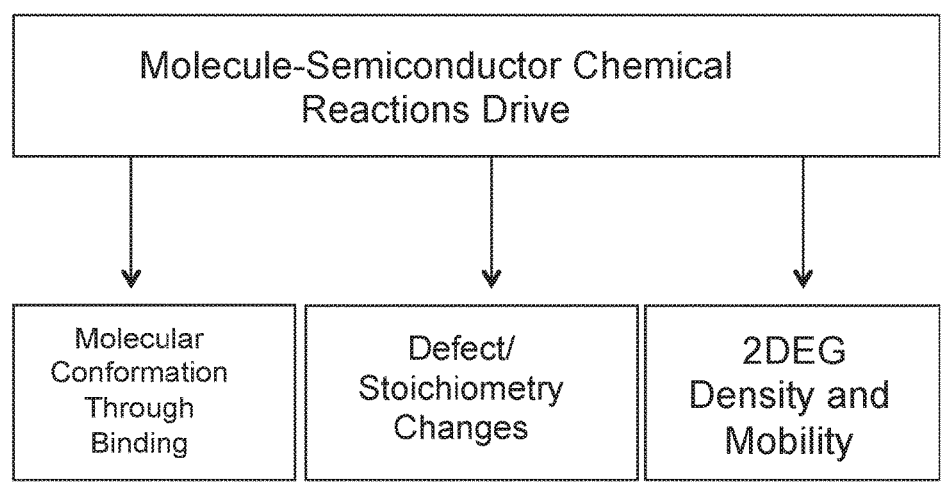
FIG. 10 shows Scheme 1 illustrating the relationships and scheme for a surfaced-based chemical reaction on the electronic platform.

The relationships and scheme for a surfaced-based chemical reaction on the electronic platform of the present invention can be shown in FIG. 10.

Surface-based chemical reactions (such as molecular binding) change the defects and stoichiometry of the oxide layer of the semiconductor material, which in turn change the 2DEG density and mobility of the semiconductor surface.

By detecting and controlling the 2DEG density via application of a bias to the device, the concentration of an analyte molecule can be determined. The conformational change of the attached analyte molecule (e.g. DNA) can be also monitored by the method disclosed herein. It is further contemplated that the process of surfaced-based chemical reactions (e.g. those depending on the availability of electrons or holes) can be monitor and modified (e.g. the reaction rate can be enhanced or inhibited) by the present invention.

The sensor of the present invention can be used in numerous applications, such as energy harvesting, catalysis, molecular synthesis, and sensing.

Various features and advantages of the invention are set forth in the following claims.

What is claimed is:

1. A sensor, comprising:
   a semiconductor layer having a two dimensional electron gas (2DEG); and
   an oxide layer in electronic contact with the semiconductor layer,
   wherein the 2DEG is present at an interface between the semiconductor layer and the oxide layer, and
   wherein the semiconductor layer comprises InAs and the oxide layer comprises In oxide and As oxide.

2. The sensor of claim 1, wherein the thickness of the oxide layer is from 0.1 nm to 10 nm.

3. The sensor of claim 1, further comprising an electronic circuit electronically coupled to the semiconductor layer, the electronic circuit measuring the electron density of the 2DEG, the electron mobility of the 2DEG, or combinations thereof.

4. The sensor of claim 1, wherein the oxide layer comprises a functionalizing molecule.

5. The sensor of claim 4, wherein the functionalizing molecule is selected from the group consisting of an oligonucleotide, a peptide, a polypeptide, a protein, a polymer, and combinations thereof.

6. The sensor of claim 1, wherein the oxide layer is deposited on the semiconductor layer.

7. The sensor of claim 1, wherein the oxide layer comprises an oxide of a material that is different from the material in the semiconductor layer.

8. A method of detecting an analyte molecule, the method comprising:
   providing a sensor comprising (a) a semiconductor layer having a two dimensional electron gas (2DEG), and (b) an oxide layer in electronic contact with the semiconductor layer, wherein the 2DEG is present at an interface between the semiconductor layer and the oxide layer, and wherein the semiconductor layer comprises InAs and the oxide layer comprises In oxide and As oxide;
   making a first measurement of an electrical property of the 2DEG;
   contacting the analyte molecule with the oxide layer of the sensor;
   subsequently making a second measurement of the electrical property of the 2DEG;
   wherein the difference between the first and second measurement of electrical property of the 2DEG indicates the presence of the analyte molecule.

9. The method of claim 8, wherein the thickness of the oxide layer is from 0.1 nm to 10 nm.

10. The method of claim 8, wherein the electrical property is selected from the group consisting of the electron density of the 2DEG, the electron mobility of the 2DEG, and combinations thereof.

11. The method of claim 8, wherein the oxide layer comprises a functionalizing molecule.

12. The method of claim 11, wherein the functionalizing molecule is selected from the group consisting of an oligonucleotide, a peptide, a polypeptide, a protein, a polymer, and combinations thereof.

13. The method of claim 8, wherein the analyte molecule is a DNA molecule.

14. The method of claim 8, wherein the oxide layer is disposed on the semiconductor layer.

15. The method of claim 8, wherein the oxide layer comprises an oxide of a material that is different from the material in the semiconductor layer.

16. The method of claim 8, wherein the electrical property of the 2DEG is measured by a Hall bar method.

17. The method of claim 8, wherein making the first measurement of the electrical property of the 2DEG includes making a measurement of the electric property under a light condition and making a measurement of the electrical property under a dark condition and then comparing the measurement under the light condition to the measurement under the dark condition, and wherein making the second measurement of the electrical property of the 2DEG includes making a measurement of the electrical property under a light condition and making a measurement of the electrical property under a dark condition and then comparing the measurement under the light condition to the measurement under the dark condition.

* * * * *